(12) United States Patent
Cauwenberghs et al.

(10) Patent No.: US 10,379,057 B2
(45) Date of Patent: Aug. 13, 2019

(54) ILLUMINATION SYSTEM, INSPECTION TOOL WITH ILLUMINATION SYSTEM, AND METHOD OF OPERATING AN ILLUMINATION SYSTEM

(71) Applicant: KLA-Tencor Corporation, Milpitas, CA (US)

(72) Inventors: Filip Cauwenberghs, Erps-Kwerps (BE); Johan DeGreeve, Brabant (BE); Pauline Begoc, Etterbeek (BE); Koen Goorman, Maastricht (NL)

(73) Assignee: KLA-Tencor Corporation, Milpitas, CA (US)

( * ) Notice: Subject to any disclaimer, the term of this patent is extended or adjusted under 35 U.S.C. 154(b) by 533 days.

(21) Appl. No.: 14/984,833

(22) Filed: Dec. 30, 2015

(65) Prior Publication Data

US 2016/0123892 A1    May 5, 2016

Related U.S. Application Data

(63) Continuation of application No. PCT/US2015/058486, filed on Oct. 30, 2015.
(Continued)

(51) Int. Cl.
*G01N 21/88* (2006.01)
*H04N 5/225* (2006.01)

(52) U.S. Cl.
CPC ....... *G01N 21/8806* (2013.01); *H04N 5/2256* (2013.01); *G01N 2021/8835* (2013.01);
(Continued)

(58) Field of Classification Search
CPC ..... G01N 21/8806; G01N 2201/06153; G01N 2201/06126; G01N 2021/8835; H04N 5/2256

See application file for complete search history.

(56) References Cited

U.S. PATENT DOCUMENTS 5,949,584 A    9/1999 White et al.
6,870,949 B2 *  3/2005 Baldwin ........... G02B 21/10
                                              356/237.3
(Continued)

FOREIGN PATENT DOCUMENTS

CN    1691278    11/2005
CN    1754175     3/2006
(Continued)

*Primary Examiner* — Hina F Ayub
*Assistant Examiner* — Amanda Merlino
(74) *Attorney, Agent, or Firm* — Simpson & Simpson, PLLC

(57) ABSTRACT

An illumination system, an inspection tool and a method for inspecting an object are disclosed. A configurable area light source is arranged in an illumination optical axis of an illumination beam path, wherein the configurable area light source is configured such that different beam diameters are settable. At least one illumination lens is positioned in the illumination beam path for directing a collimated beam at least onto a field of view on a surface of the object, wherein a value of an angle of incidence of the illumination optical axis of the illumination beam path equals a value of an angle of reflectance of the imaging optical axis of the imaging beam path. The invention allows the combination of the functionality of a wide angle coaxial illumination and a collimated coaxial illumination in one illumination system.

42 Claims, 10 Drawing Sheets

Related U.S. Application Data

(60) Provisional application No. 62/073,393, filed on Oct. 31, 2014.

(52) U.S. Cl.
CPC .............. *G01N 2201/06126* (2013.01); *G01N 2201/06153* (2013.01)

(56) References Cited

U.S. PATENT DOCUMENTS

| | | | |
|---|---|---|---|
| 7,352,467 | B2 | 4/2008 | Chinowsky |
| 7,738,092 | B1 | 6/2010 | Stokowski |
| 2004/0042001 | A1 | 3/2004 | Vaez-Iravani et al. |
| 2013/0321797 | A1 | 12/2013 | Cavan et al. |
| 2014/0375987 | A1* | 12/2014 | Brunner ............. G01N 21/8806 356/237.5 |

FOREIGN PATENT DOCUMENTS

| | | |
|---|---|---|
| JP | 2011-106912 | 6/2011 |
| JP | 2013-140032 | 7/2013 |
| JP | 2013-145123 | 7/2013 |
| TW | 201350837 | 3/2005 |
| WO | 2009148862 A2 | 12/2009 |
| WO | 2010029549 A1 | 3/2010 |

\* cited by examiner

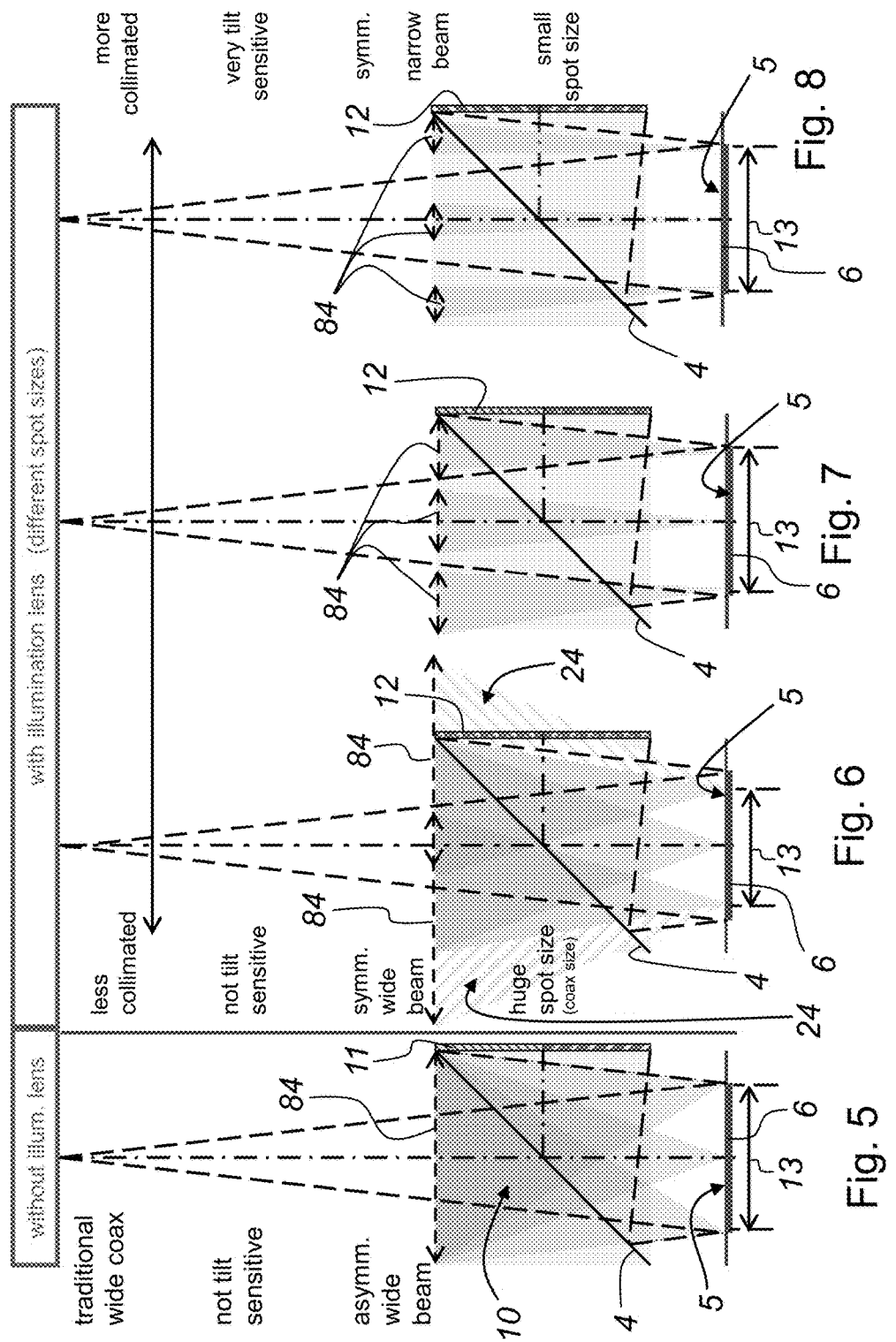

ional Application No. 62/073,393, filed Oct. 31, 2014, which applications are incorporated herein by reference in their entirety.

ILLUMINATION SYSTEM, INSPECTION TOOL WITH ILLUMINATION SYSTEM, AND METHOD OF OPERATING AN ILLUMINATION SYSTEM

CROSS REFERENCE TO RELATED APPLICATIONS

This application is filed under 35 U.S.C. § 111(a) and § 365(c) as a continuation of International Patent Application No. PCT/US2015/058486 filed Oct. 30, 2015 which application claims the benefit of U.S. Provisional Application No. 62/073,393, filed Oct. 31, 2014, which applications are incorporated herein by reference in their entirety.

FIELD OF THE INVENTION

The present invention refers to an illumination system.

Furthermore, the present invention refers to an inspection tool with an illumination system.

Additionally, the present invention refers to a method of operating an illumination system.

BACKGROUND OF THE INVENTION

Japanese patent application JP 2013-145123 A discloses a wide-angle reflection optical system with coaxial illumination. The optical system has a camera for forming an image of an object to be inspected on an area sensor of the camera. A branch optical element is disposed rearward a lens, which is close to the object side to be inspected. The branch optical element is located on an optical axis of the optical system. A light source is provided for coaxial illumination of the inspection object. The illumination luminous flux from the light source enters the branch optical element from a direction so that it crosses the optical axis of the image capture optical system.

Japanese patent application JP 2011-106912 A discloses an imaging illumination device that uses coaxial illumination to capture a bright image with an element to be imaged. The illumination light irradiated from a light source is made incident to a half mirror via a diffusion plate. A portion of the light is reflected and illuminates a substrate. A portion of the light reflected by the substrate passes through the half mirror and is incident on the imaging element of an imaging device. The pattern image formed on the substrate is photographed. A reflecting member (mirror) that totally reflects the illumination light to the object to be illuminated is fixed to the outside of the portion of the half mirror, where the image of an imaging object (imaging area) passes through and the incident side of the illumination light. The illumination light from the light source is reflected by the half mirror and has the substrate that is reflected by this reflecting member irradiated. As a result, the substrate (object to be illuminated) can be illuminated brightly.

SUMMARY OF THE INVENTION

It is an object of the invention to provide an illumination system which enables different illumination conditions in one physical setup, and the different illumination conditions should be selected in real time.

The above object is achieved by an illumination system for collimated illumination. The illumination system comprises:

a configurable area light source arranged in an optical axis of an illumination beam path, wherein the area light source is configured such that different beam diameters are settable; an optical axis of an imaging beam path; and at least one illumination lens is positioned in the illumination beam path for directing a collimated beam onto at least a field of view on a surface of an object, wherein a value of an angle of incidence of the optical axis of the illumination beam path equals a value of an angle of reflectance of the optical axis of the imaging beam path.

A further object of the invention is to provide an inspection tool which enables the inspection of objects with different illumination conditions in one physical setup and the different illumination conditions for the object under inspection should be selected in real time.

The above object is solved by an inspection tool which comprises:

a camera, arranged in an optical axis of an imaging beam path;

an imaging lens positioned in the imaging beam path for imaging at least a portion of a surface of an object into an image plane of the camera;

an illumination system with a configurable area light source, wherein the configurable area light source is arranged in an optical axis of an illumination beam path and the configurable area light source is configured such that different beam diameters are settable; and at least one illumination lens is positioned in the illumination beam path for directing a collimated beam onto a field of view on the surface of the object, wherein a value of an angle of incidence of the optical axis of the illumination beam path equals a value of an angle of reflectance of the optical axis of the imaging beam path.

An additional object of the invention is to provide a method for inspecting an object with different illumination conditions in one physical setup and the different illumination conditions (wide beam coaxial light and all collimation angles) for the object under inspection should be selected in real time.

The above object is achieved by a method for inspecting an object wherein the method comprises:

a. directing illumination light, defining a light beam opening angle, from a configurable area light source via an illumination lens along an illumination beam path onto a surface of an object;

b. directing reflected light from the surface of the object along an imaging beam path c. imaging the reflected light from the surface of the object with an imaging lens onto an image plane of a camera;

d. changing the diameter of the illumination light and thereby changing the opening angle of the light beam; and e. repeating the steps a-d for generating in real time images of a field of view of the surface of the object with different beam opening angles and collimation angles, respectively.

The advantage of the inventive illumination system, the inventive inspection tool and the inventive method are that the collimation angle is selectable at real time (e.g. when different collimation angles are desired for different consecutive camera images). This is achieved because all wide beam coaxial light and all collimation angles are combined in one physical setup. According to the invention it is possible to combine the functionality of a wide angle coaxial illumination and a collimated coaxial illumination in one illumination system. Instead of using a point light source, an area light source is used on which different area diameters can be selected or addressed.

For example, if a very small area diameter is selected with the area light source, the illumination is comparable to the point light source functionality. This results in a very narrow beam and collimated coaxial illumination.

In case the complete area of the area light source is selected, this selection is comparable to putting the "diffuse area light source" from a "wide angle coaxial illumination" at the location of the "point light source" of a collimated coaxial illumination. The result of this setup is a very wide beam coaxial illumination which is comparable to the light coming from a traditional "wide angle coaxial illumination" and the exception is that the light is now projected through the illumination lens.

In case any area diameter of the area light source is used between the complete area diameter and the very small area diameter of the area light source, a variation of the collimation beam opening angle is possible.

The inventive illumination system allows an additional setup, which is that only the outer diameters of the area light source are used. This setup results in a dark field near coaxial illumination.

The illumination lens of the inventive illumination system is a Fresnel lens. Although according to one embodiment the illumination lens of the present invention is a Fresnel lens, it will be clear to those skilled in the art that the illumination lens is not limited to a Fresnel lens.

According to an embodiment of the illumination system, a beam splitter is positioned in the illumination beam path after the at least one illumination lens. The beam splitter directs the collimated illumination light (illumination condition selected according to the addressed areas of the area light source) from the area light source along a redirected optical axis of the illumination beam path onto the surface of the object. With the use of the beam splitter the arrangement of the optical axis of the imaging beam path is coaxial with the redirected optical axis of the illumination beam path.

It is obvious for a skilled person that the same effect may be achieved by swapping the imaging beam path and the illumination beam path to the opposite side of the beam splitter. Here the illumination beam path goes direct through the beam splitter. The imaging beam path is now folded (reflected) by the beam splitter.

The area light source is a 2-dimensional arrangement of a plurality of discrete light emitting elements. According to one possible embodiment the discrete light emitting elements are light emitting diodes. The 2-dimensional arrangement of the plurality of light emitting elements is a matrix device assigned to the configurable area light source. With the control and drive device it is possible to address the light emitting elements in such a way that concentric geometrical shapes on the area light source emit light. Another possible embodiment of the configurable area light source comprises at least one homogeneous light emitting element and at least one configurable shutter element, which is arranged downstream of the at least one homogeneous light emitting element in the illumination beam path. One possibility for a configurable shutter element is an LCD-screen which covers the light source. The LCD pixels are used for blocking the light. The finer pitch of the LCD-screen allows more flexibility in projected patterns. According to a further embodiment, the configurable area light source comprises a single light emitting element, providing a homogeneous area lighting. The LCD-screen is positioned in front of the single light emitting element. The LCD-screen comprises a plurality of individual pixels, which are arranged in a 2-dimensional arrangement. The individual pixels are addressable in order to change a transmittance value of each individual pixel.

Another possibility is that the configurable area light source is configured as an arrangement of light emitting elements on a carrier in the form of concentric geometrical shapes. An ideal solution for the concentric geometrical shapes (addressable or already arranged) is concentric circles. Another possibility of the concentric geometrical shapes is a plurality of concentric rectangles. This arrangement would be the easiest solution (for instance LED positioning), but the collimation angles are different for the diagonal direction versus the horizontal/vertical direction of the rectangle. A good compromise could be to use concentric hexagons, which can be realized for example by a staggered grid of light emitting elements (LED grid).

However, the design of the area light source can be such that in fact any pattern can be projected. This will result in light beams having a light beam opening angle corresponding to that pattern. It has to be understood that the configuration of the area light source is not limited to concentric geometrical shapes. It is understood by a skilled person that the projected pattern of the area light source is not limited to concentric geometrical shapes. According to the invention any pattern can be projected. The individual light emitting elements can be addressed by a computer or a control and drive device so that the desired pattern is achieved. According to another embodiment of the invention the pixels of an LCD screen, covering the single area light source, are addressed individually (addressed LCD pixels block the light from the area light source), so that any desired pattern can be projected.

An additional inventive concept is the integration of the inventive configurable area light source into an inspection tool. A camera is arranged in an optical axis of an imaging beam path. An imaging lens is positioned in the image beam path for imaging at least a portion of a surface of an object into an image plane of the camera. An illumination system with an area light source is arranged in an optical axis of an illumination beam path. The configurable area light source is configured such that different beam diameters for illumination are settable. At least one illumination lens is positioned in the illumination beam path for directing a collimated beam onto a field of view on the surface of the object, wherein a value of an angle of incidence of the optical axis of the illumination beam path equals a value of an angle of reflectance of the optical axis of the imaging beam path. This condition is true as well in case a beam splitter is positioned in the illumination beam path after the at least one illumination lens. The beam splitter directs the collimated illumination light from the area light source along a redirected optical axis of the illumination beam path, which is parallel to the imaging beam path, onto the surface of the object. Consequently, the optical axis of the imaging beam path is coaxial with the redirected optical axis of the illumination beam path.

By replacing the spot light source with a light source which can emit a light beam with different diameters, an inspection tool with a configurable illumination, for example configurable light beam opening angles, is possible. The configuration of the light beam opening angle ranges from collimated light beams up to wide opening angle light beams. The different light diameters or shapes can be switched on in real time as independent channels. This leaves the possibility to change for instance the collimation angle of the illumination for consecutive camera images.

The beam splitter of the inventive illumination system is mounted in a holder. An object to be inspected faces with its surface a first side face of the holder. A mirror is mounted to a second side face of said holder such that light from the configurable area light source is directed via the illumination lens onto the beam splitter and from there onto the surface of the object.

The advantage of providing different light beam opening angles in one coaxial illumination setup and thus in one inspection tool is that a user can carry out several different inspection routines with one and the same tool.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

Below, the invention and its advantages will be further described with reference to the accompanying figures in which:

FIG. 5 is a schematic view of the degree of the collimation beam opening angle of the light from an area light source without the use of an illumination lens.

FIG. 6 is a schematic view of the degree of the collimation beam opening angle of the light from a configurable area light source, wherein the illumination system provides a huge spot size from the area light source in combination with the illumination lens.

FIG. 7 is a schematic view of the degree of the collimation beam opening angle of the light from a configurable area light source, wherein the illumination system provides an intermediate spot size from the area light source in combination with the illumination lens.

FIG. 8 is a schematic view of the degree of the collimation beam opening angle of the light from a configurable area light source wherein the illumination system provides a small spot size from the area light source in combination with the illumination lens.

DETAILED DESCRIPTION OF THE INVENTION

Figure 1:
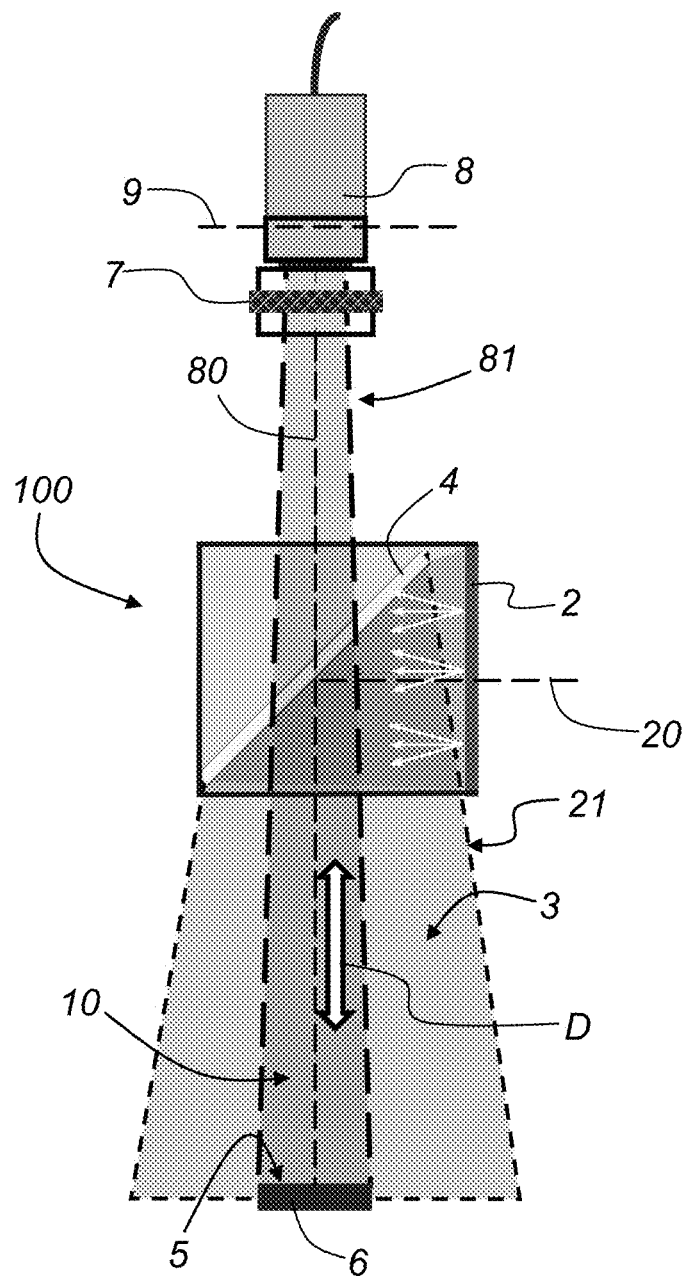
FIG. 1 is a schematic view of a prior art wide angle coaxial illumination system using a big diffuse light source.

In the figures like reference numerals are used for like elements or elements of like function. Furthermore, for the sake of clarity, only those reference numerals are shown in the figures which are necessary for discussing the respective figure.

FIG. 1 is a schematic view of a prior art illumination system 100 which is configured as wide angle coaxial illumination system 100 using a big diffuse area light source 2. The working principle of the wide angle coaxial illumination system 100 is that the big diffuse area light source 2 projects its light 3 via a beam splitter 4 towards a surface 5 of an object 6. The light source 2 is arranged in an optical axis 20 of an illumination beam path 21. The illumination system 100 is a coaxial illumination system 100, because downstream from the beam splitter 4 the light 3 from the light source 2 has the same approximate direction D as an imaging optical axis 80 of an imaging beam path 81. A camera 8 is arranged in the imaging optical axis 80 of the imaging beam path 81. An imaging lens 7 images a portion or field of view of the surface 5 of the object 6 onto an image plane 9 of the camera 8. The light 10 reflected from the surface 5 of the object 6 travels along the imaging optical axis 80 of the imaging beam path 81 and, after passing the beam splitter 4, reaches the imaging lens 7 of the camera 8.

Figure 2:
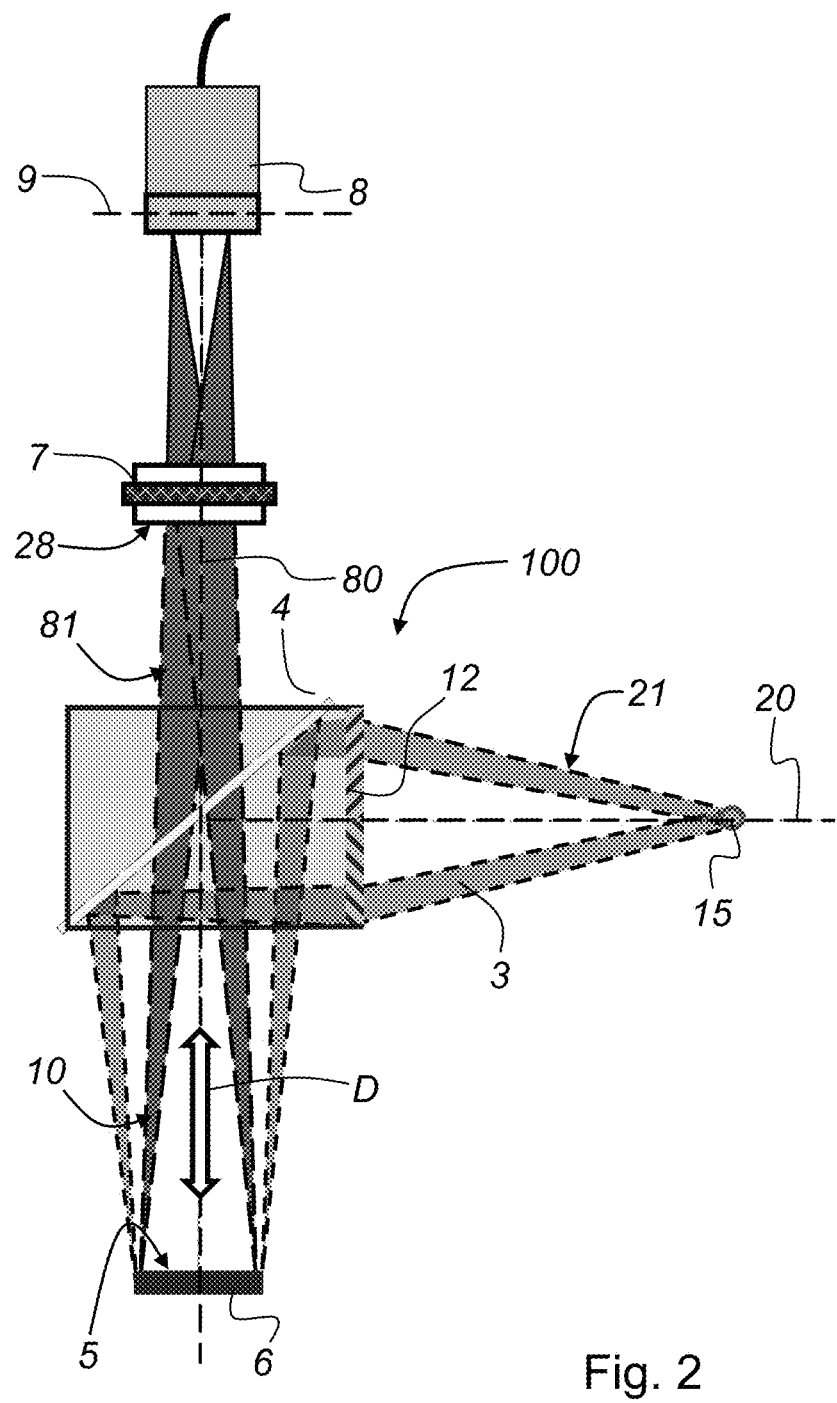
FIG. 2 is a schematic view of a prior art collimated coaxial illumination system using a point light source.

FIG. 2 is a schematic view of a prior art illumination system 100, which is configured as a collimated coaxial illumination system 100 using a point light source 15. In order to obtain the collimated coaxial illumination, a point light source 15 is projected by an illumination lens 12 via beam splitter 4 towards surface 5 of object 6. The point light source 15 is arranged in an optical axis 20 of an illumination beam path 21. The illumination system 100 is a collimated coaxial illumination system 100, because downstream from the beam splitter 4 the light 3 from the point light source 15 has the same approximate direction D as an imaging optical axis 80 of an imaging beam path 81 and is focused on the aperture 83 of the imaging lens 7 (provided the object 6 is a mirror-like device). The camera 8 is arranged in the imaging optical axis 80 of the imaging beam path 81. In case the object 6 would be a mirror, the point light source 15 would be projected and focused exactly on the lens pupil (aperture) 83 (see FIG. 3) of the imaging lens 7. This is the case if the imaging lens 7 is a perspective lens. In case the imaging lens 7 is a telecentric lens, the point light source 15 would be projected to infinity.

The imaging lens 7 images a portion or field of view of the surface 5 of the object 6 onto an image plane 9 of the camera 8. The light 10 reflected from the surface 5 of the object 6 travels along the imaging optical axis 80 of an imaging beam path 81 and, after passing the beam splitter 4, reaches the imaging lens 7 of the camera 8.

Figure 3:
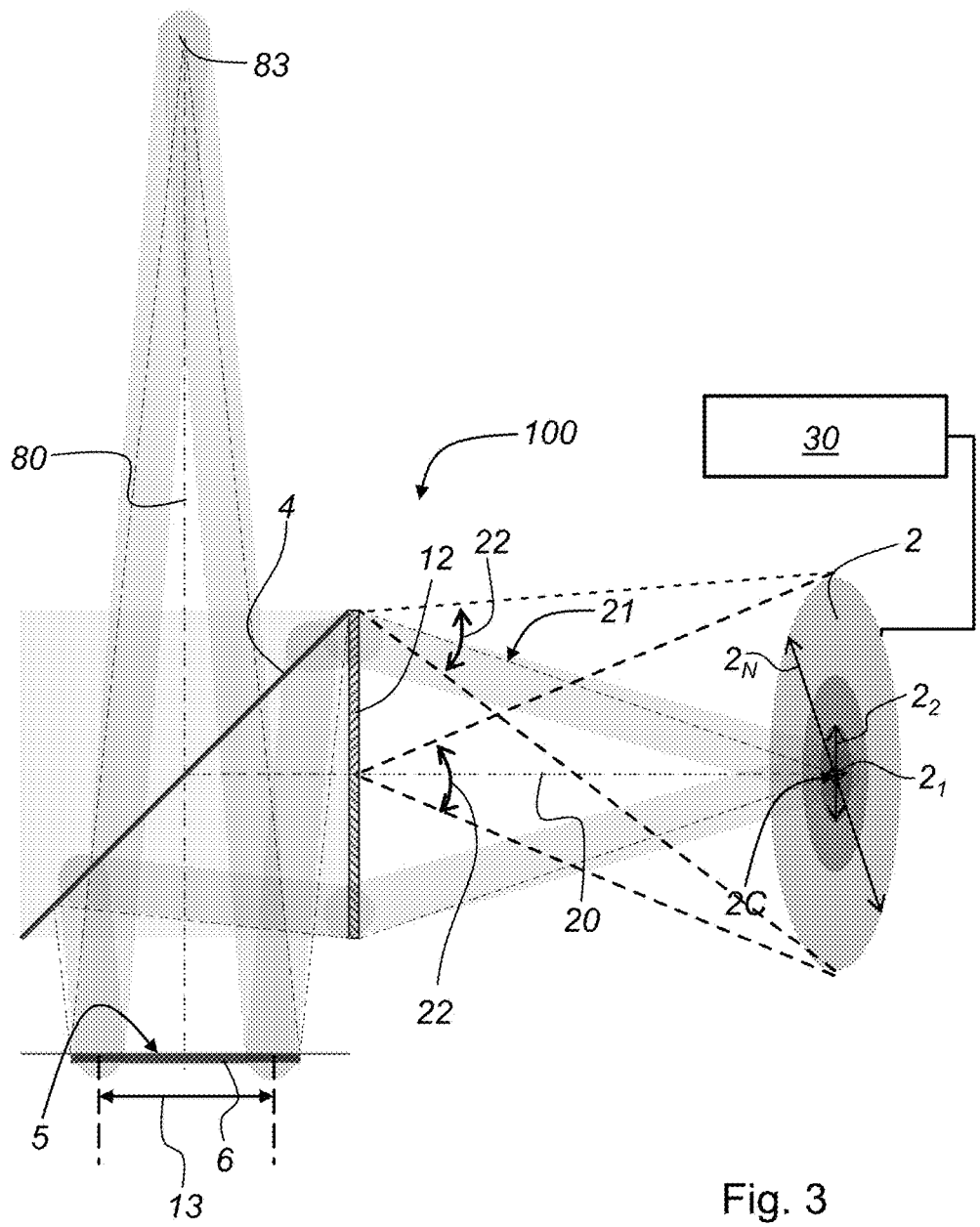
FIG. 3 is a schematic view of an inventive concept of a collimated coaxial illumination system.

FIG. 3 is a schematic view of an embodiment of the inventive concept for an illumination system 100, which is a collimated coaxial illumination system 100. The inventive illumination system 100 combines the functionality of a wide angle coaxial illumination and a collimated coaxial illumination in one area light source 2. The configurable area light source 2 is configured such that different area diameters $2_1, 2_2, \ldots, 2_N$ can be selected or initialized. In case of a very small area diameter, like area diameter $2_1$, the illumination system 100 is comparable to the illumination system 100 of FIG. 2 using the point light source functionality. The selection of the smallest area diameter 2₁ results in very narrow beam of collimated coaxial illumination.

In case the complete area, the largest area diameter 2_N, of the configurable area light source 2 is selected or initialized, the set-up is comparable to the set-up with the diffuse area light source 2 of FIG. 1 wherein the diffuse area light source 2 is at the location of the point light source 15 of FIG. 2. The result is a collimated coaxial illumination having a very wide beam coaxial illumination. This illumination is comparable to the light coming from a traditional "wide angle coaxial illumination". According to the invention the light from the configurable area light source 2 is projected now through the illumination lens 12 onto the beam splitter 4 and from there onto the surface 5 of the sample 6.

The area light source 2 is arranged in the optical axis 20 of the illumination beam path 21. As mentioned before, the configurable area light source 2 is configured such that the different settable area diameters $2_1, 2_2, \ldots, 2_N$ result in different beam diameters. Any area diameter $2_1, 2_2, \ldots, 2_N$ between the smallest diameter $2_1$ and the largest area diameter $2_N$ allows a variation of the collimation beam opening angle 22.

In case the configurable area light source 2 is set such that only the outer area diameters $2_2, \ldots, 2_N$ are used (send out light) a dark spot remains in the center 2C of the configurable area light source 2. This set-up results in a dark field near coaxial illumination.

The illumination lens 12 in the illumination beam path 21 illuminates a collimated beam onto a field of view 13 on the surface 5 of the object 6. From the surface 5 of the object 6 the field of view 13 is imaged along the imaging optical axis 80 of imaging beam path 81 onto the imaging lens pupil (aperture) 83 of the imaging lens (imaging lens and camera not shown here).

Figure 4:
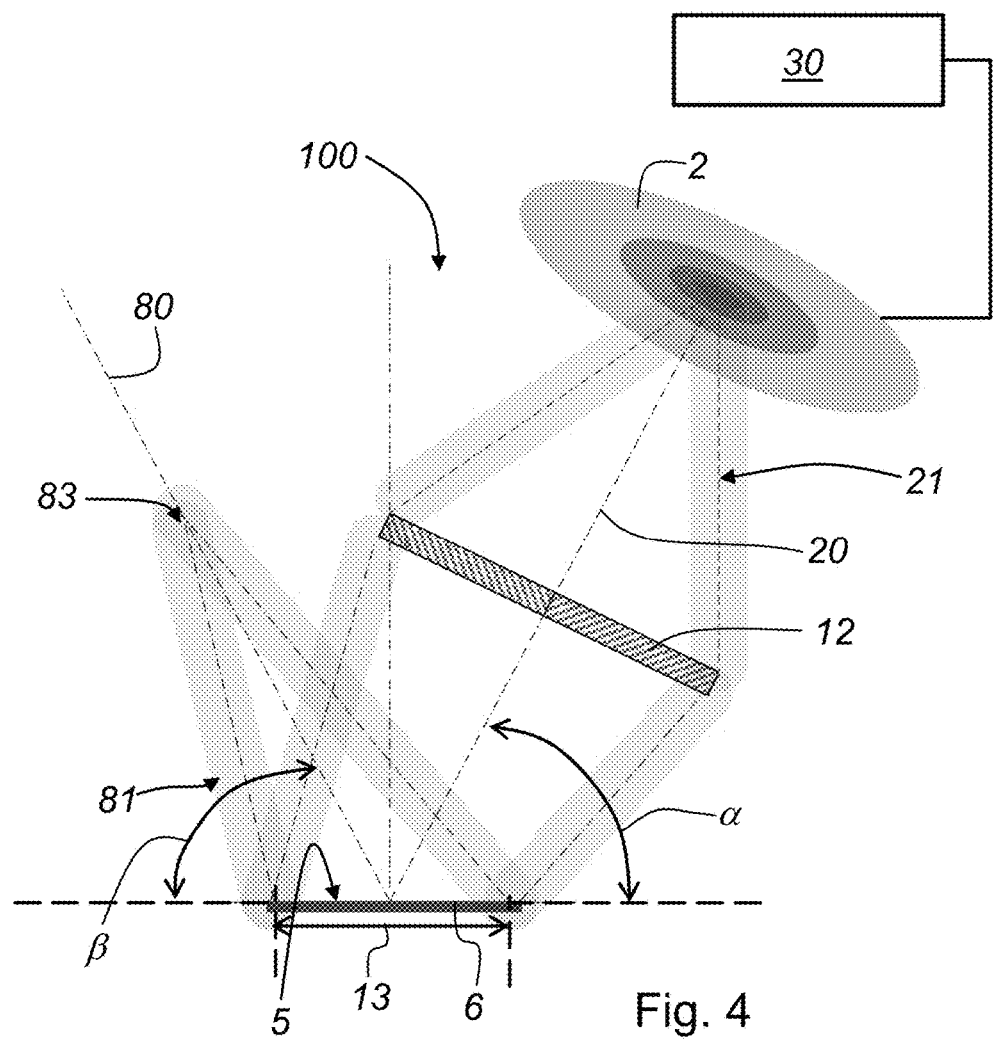
FIG. 4 is a schematic view of an inventive concept of a collimated illumination system.

FIG. 4 is a schematic view of a further embodiment of the inventive concept for an illumination system 100. The beam splitter 4 is omitted. The configurable area light source 2 is arranged such that the optical axis 20 of the illumination beam path 21 is tilted at an angle α with respect to surface 5 of the object 6. As mentioned above, the light from the area light source 2 is imaged by the illumination lens 12 onto the surface 5 of the object 6. The light reflected from the surface 5 of the object 6 propagates along the imaging optical axis 80 of the illumination beam path 81. The field of view 13 on the surface 5 of the object 6 is imaged onto the imaging lens pupil (aperture) 83 (imaging lens and camera not shown). The imaging optical axis 80 of the imaging beam path 81 is tilted at an angle β with respect to the surface 5 of the object 6. The optical setup of the illumination system 100 is such that the value of an angle α of the optical axis 20 of the illumination beam path 21 equals the value of an angle β of the imaging optical axis 80 of the imaging beam path 81. The bright field illumination is achieved without the use of the beam splitter. In other words: an inspection tool where the value of the illumination angle α equals the value of the imaging angle β.

FIG. 5 is a schematic view of the value degree of the collimation beam opening angle 84 without the use of an illumination lens 12. Instead of the illumination lens 12 a diffuser plate 11 of an area light source (nor shown here) is positioned prior to the beam splitter 4. As a result from the illumination of the object 6 with a wide beam and without an illumination lens 12 one obtains an asymmetric wide beam which is a traditional wide coaxial illumination. Because of the wide beam opening angle 22 (see FIG. 3) the imaging quality of the object 6 in the camera 8 will not be sensitive to a tilt of surface 5 of object.

FIG. 6 to FIG. 8 show the dependence of the collimation beam opening angle 84 from the spot size (area diameter) of the illumination light. FIG. 6 is a schematic view of the degree of collimation beam opening angle 84 using a configurable area light source 2 with a huge spot size (huge area diameter) and an illumination lens 12. Due to the huge spot size (huge area diameter) set by the configurable area light source a portion 24 of the collimation beam opening angle 84 is cut off. This makes the beam opening angle 84 asymmetrical towards the edges of the field of view 13. The light, reflected from the surface 5 of the object 6, is not sensitive to a tilt of the beam splitter 4. FIG. 7 is a schematic view of the degree of collimation beam opening angle 84 using a configurable area light source with an intermediate spot size (reduced spot size compared to FIG. 6). From the illumination lens 12 the light from the configurable area light source is collimated via the beam splitter 4 onto the surface 5 of the object 6. From FIG. 7 it is clear that with the reduced spot size the collimation beam opening angle 84 becomes narrower. Additionally, the light reflected from the surface 5 of the object 6 is now sensitive to a tilt of the surface 5 object 6. FIG. 8 is a schematic view of the degree of collimation beam opening angle 84. Compared with the schematic view of FIG. 7 the spot size is reduced further. The configurable area light source 2 has now a small spot size (small area diameter). The result of the narrow beam opening angle is that the set-up of the illumination system is very sensitive to the tilt of the surface 5 of the object 6. Additionally, the light reflected from the surface 5 of the object 6 becomes more collimated compared with the spot sizes (area diameters) shown in FIG. 6 or 7.

Figure 9:
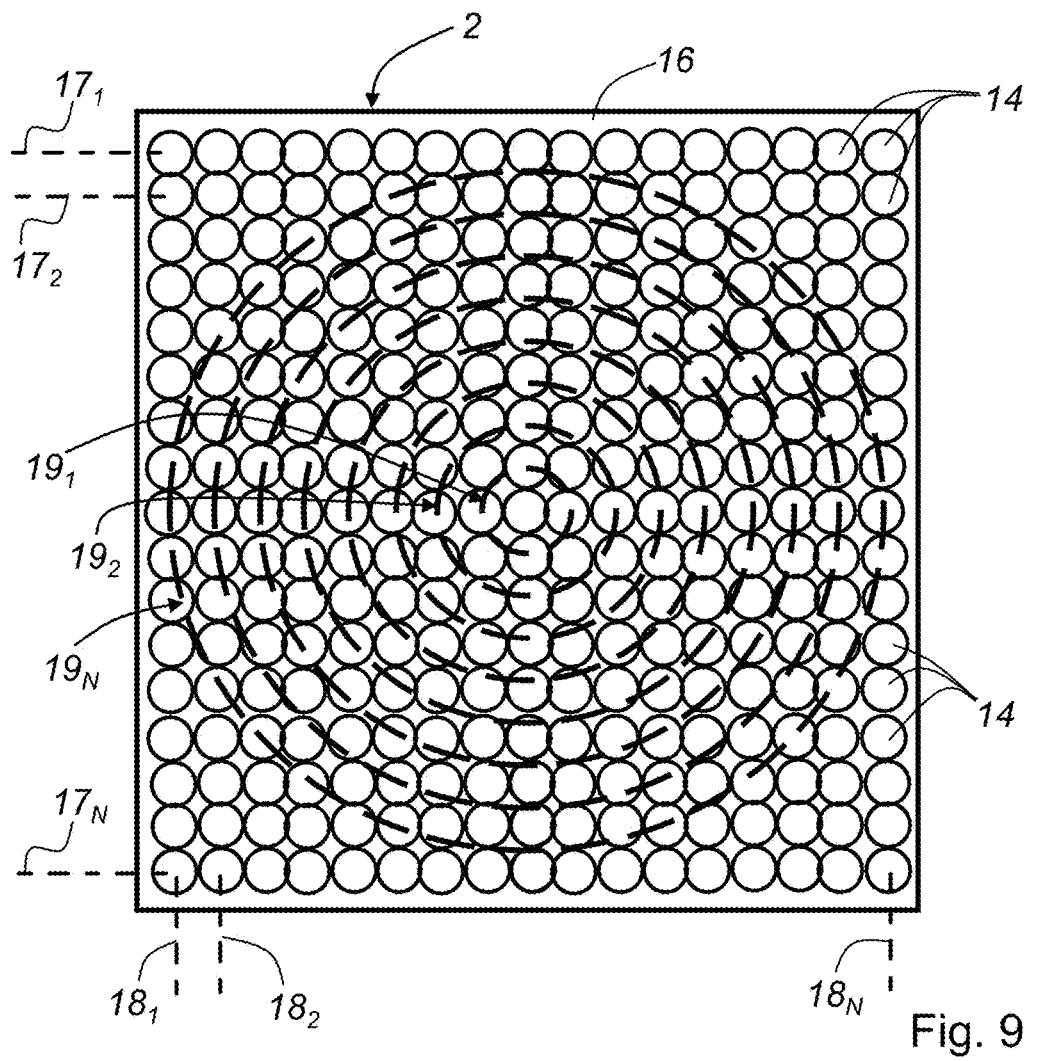
FIG. 9 is a top view of an embodiment of a configurable area light source.

FIG. 9 is a top view of an embodiment of a configurable area light source 2. In the embodiment shown here, the area light source 2 is configured by a plurality of light emitting elements 14, which are arranged in a 2-dimensional manner on a carrier 16. Here the light emitting elements 14 are arranged in rows $17_1, 17_2, \ldots, 17_N$ and columns $18_1, 18_2, \ldots, 18_N$ and thereby form a matrix. According to one possible embodiment, the light emitting elements 14 are light emitting diodes (LEDs). As shown in FIGS. 3 and 4, the configurable area light source 2 is assigned to a control and drive device 30, or any embedded system which can address the area light source 2 accordingly. With the control and drive device 30 it is possible to address the individual light emitting elements 14 and generate different light emitting shapes and/or sizes of the configurable area light source 2. FIG. 9 shows one embodiment how the different sizes $19_1, 19_2, \ldots, 19_N$ of the configurable area light source 2 are initialized. The light emitting elements 14 are addressed by the control and drive device 30 such that various sizes of the circles of the area light source 2 are addressed. It has to be noted that the addressable form of circles of the configurable area light source 2 should not be considered as a limiting factor.

Figure 10:
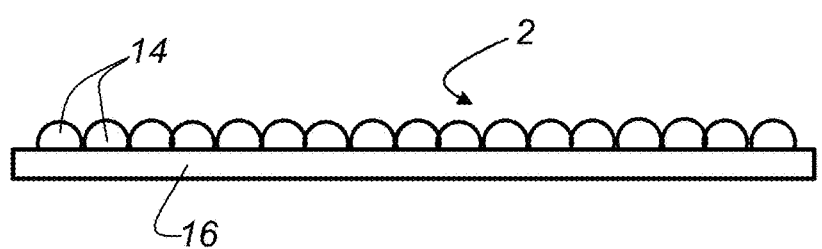
FIG. 10 is a side view of the embodiment of the configurable area light source of FIG. 9.

FIG. 10 is a side view of the embodiment of the configurable area light source 2 of FIG. 9. The light emitting elements 14 are arranged on the carrier 16. The configurable area light source 2 in addition can be provided with a diffuser (not shown) in order to achieve a uniform light distribution (area) of the addressed light emitting elements 14 on the carrier 16.

The configurable area light source 2 can typically be an area made of concentric geometrical shapes 23. The ideal solution would be to use concentric circles 25. This embodiment is shown in FIG. 11, wherein the configurable area light source 2 is formed by the light emitting elements 14 already positioned in the shape of the concentric circles 25.

Figure 12:
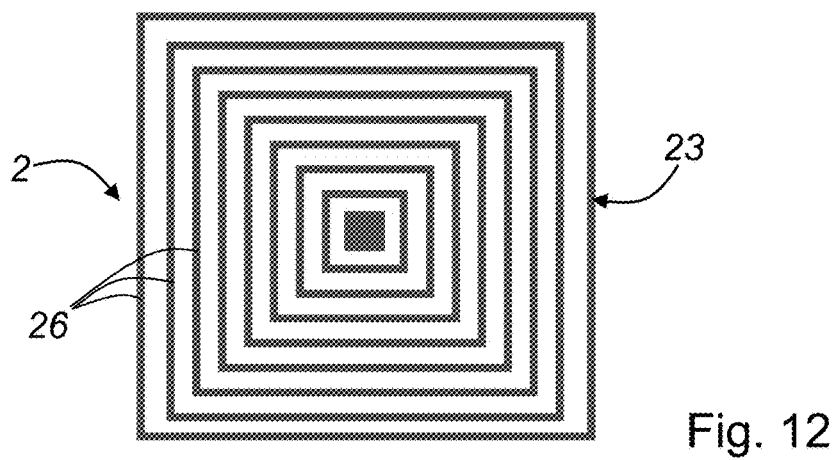
FIG. 12 shows another embodiment of a configurable area light source.

FIG. 12 shows another embodiment of a configurable area light source 2. The easiest solution for the positioning of the light emitting elements 14 would be to use concentric rectangles 26. The geometrical shapes 23 are rectangles, which have the drawback that the collimation angles are different for the diagonal direction versus the horizontal/vertical direction of the rectangles.

Figure 13:
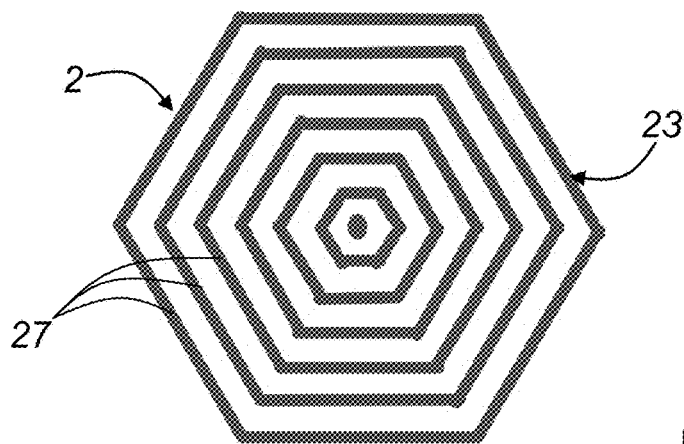
FIG. 13 shows a further embodiment of a configurable area light source.

FIG. 13 shows a further embodiment of a configurable area light source 2. A good compromise, compared with the embodiment shown in FIG. 12, is to use concentric hexagons 27 as the concentric shapes 23. This may be achieved for example by making a staggered grid of light emitting elements 14 (not shown here).

Figure 11:
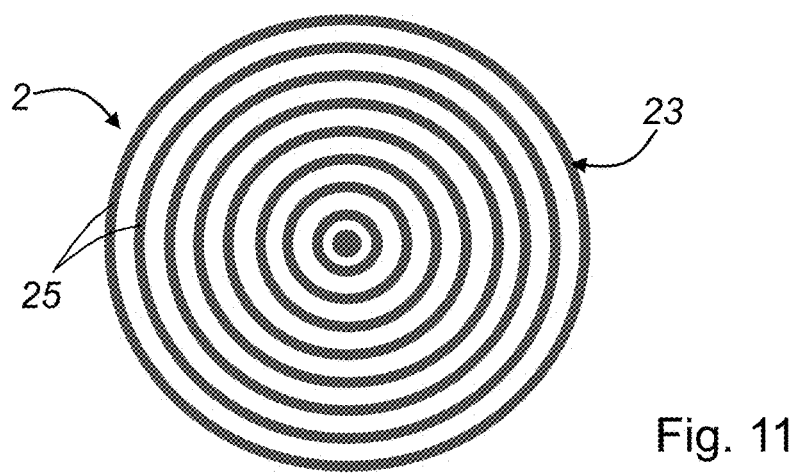
FIG. 11 shows one embodiment of a configurable area light source.

However, the design of the area light source is not limited to concentric geometrical shapes 23 shown in FIGS. 11 to 13. In fact any pattern can be projected by addressing the light emitting elements 14 of the area light source 2. This will result in light beams having the desired pattern and the desired light beam opening angle.

Figure 14:
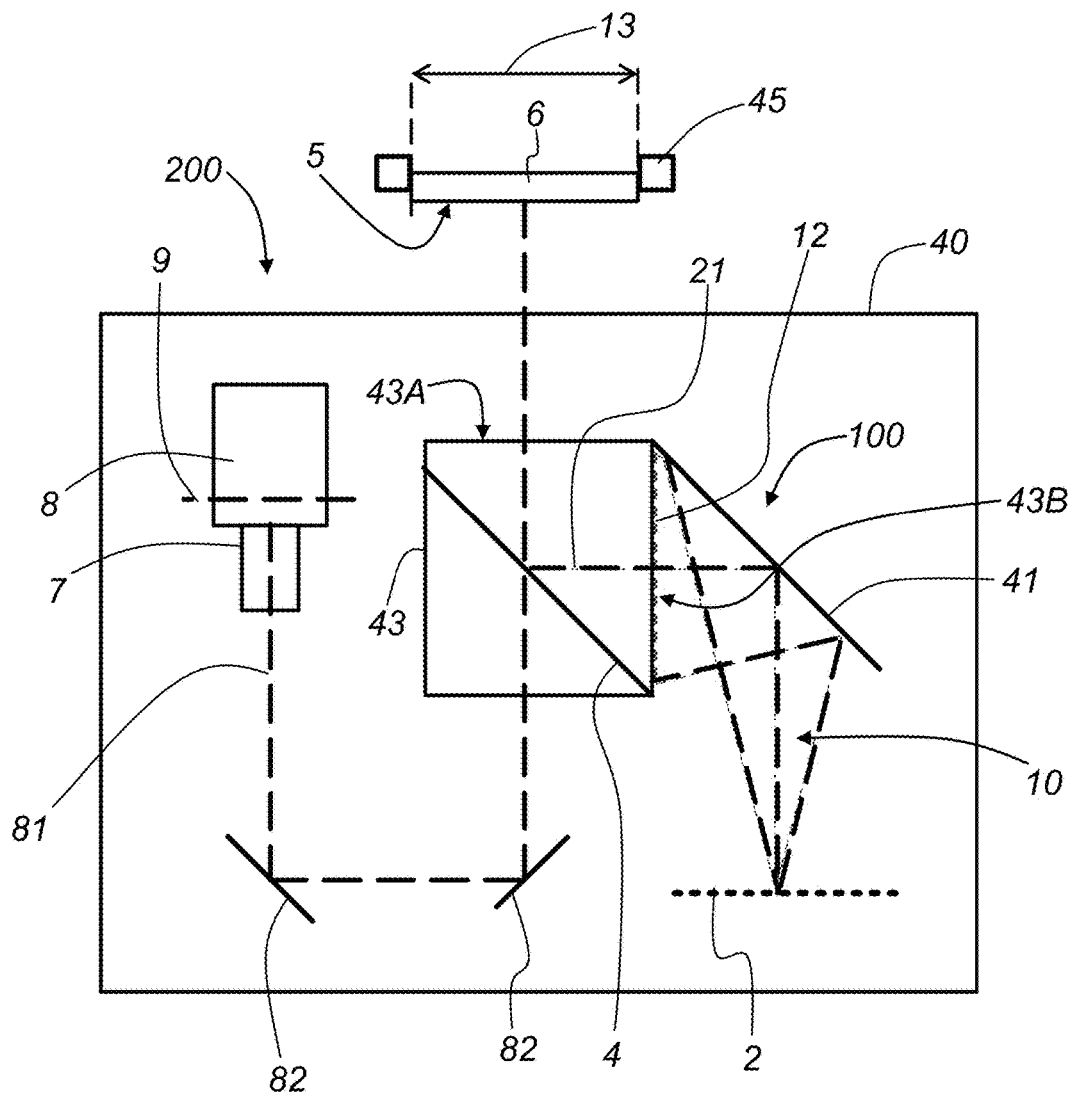
FIG. 14 shows the integration of the inventive illumination system into an inspection tool or apparatus.

FIG. 14 shows a possible embodiment of the integration of the inventive illumination system 100 into an inspection apparatus 200. The inventive illumination system 100 is integrated in an existing housing 40 of the inspection apparatus 200. The inventive illumination system 100 provides different light beam opening angles in one coaxial illumination setup. The light 10 from the configurable area light source 2 is directed via a mirror 41 to the illumination lens 12 (one possible embodiment of the illumination lens 12 is a Fresnel lens). The mirror 41 is necessary for folding illumination beam path 21. This saves space and enables the integration of the illumination system 100 into the inspection apparatus 200.

The beam splitter 4 of the inventive illumination system 100 is mounted in a holder 43. The object 6, to be inspected, is held by a carrier 45 so that the surface 5 of the object 6 faces a first side face 43A of the holder 43. The mirror 41 is mounted to a second side face 43B of the holder 43 such that illumination light 10 from the configurable area light source 2 is directed via the illumination lens 12 onto the beam splitter 4 and from there onto the surface 5 of the object 6.

The light reflected from the surface 5 of the object 6 travels along the imaging beam path 81 to the camera 8. The imaging lens 7 images a field of view 13 of the surface 5 of the object 6 into the image plane 9 of the camera 8. In the embodiment shown here, two additional mirrors 82 are provided in the imaging beam path 81, in order to fold the imaging beam path 81 for space reasons. With the inventive inspection apparatus 200 it is possible to provide different light beam opening angles in one coaxial illumination setup.

Figure 15:
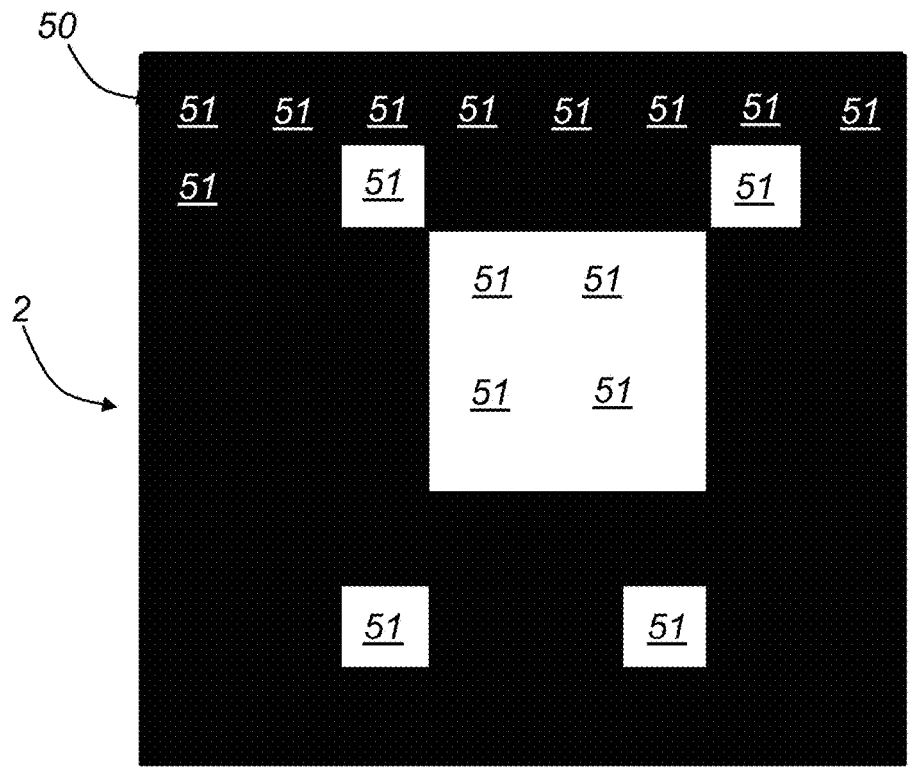
FIG. 15 is a top view of a further embodiment of the configurable area light source, wherein a LCD is used for forming the illumination pattern.
Figure 16:
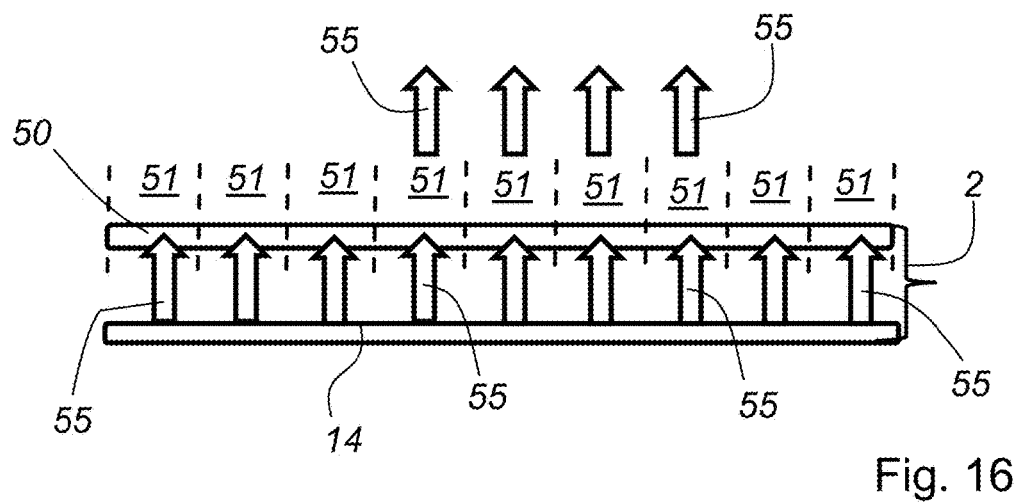
FIG. 16 is a side view of the embodiment of the configurable area light source of FIG. 15.

FIG. 15 shows an additional embodiment of a configurable area light source 2. A LCD-screen 50 is positioned after at least one light emitting element 14. In the embodiment shown here, a single light emitting element 14 is used which provides a homogeneous area lighting of the back of the LCD 50 (see the side view configurable area light source 2 as shown in FIG. 16). The plurality of pixels 51 of the LCD 50 can be addressed individually. The LCD 50 comprises a plurality of pixels 51, arranged in a 2-dimensional manner. Accordingly, various illumination patterns can be formed by addressing the pixels 51 individually by a known control device (not shown). The pixels 51 of the configurable area light source 2 (see FIG. 15) are addressed in a manner , so that a group of pixels block the light 55 from the light emitting element 14 completely and the other pixels 51 let the light 55 from the light emitting element 14 pass (see FIG. 16). It is evident for a skilled person that the transmittance of the individual pixels 51 can be adjusted as well.

Figure 17:
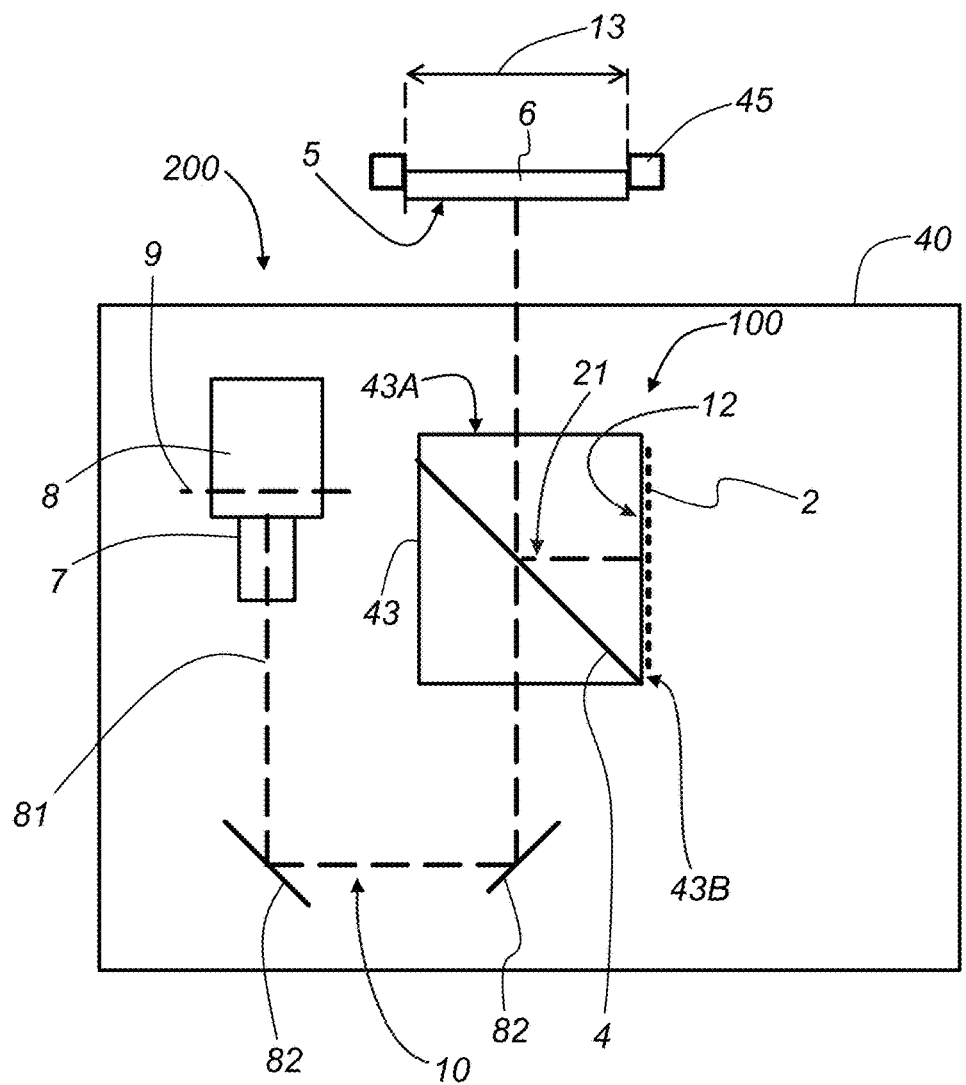
FIG. 17 shows another example embodiment of the integration of the inventive illumination system into an inspection tool or apparatus.

FIG. 17 shows another possible embodiment of the integration of the inventive illumination system 100 into an inspection apparatus 200. The inventive illumination system 100 is integrated in an existing housing 40 of the inspection apparatus 200. The inventive illumination system 100 provides different light beam opening angles in one coaxial illumination setup. The light 10 from the configurable area light source 2 is directed to the illumination lens 12 (one possible embodiment of the illumination lens 12 is a Fresnel lens). The beam splitter 4 of the inventive illumination system 100 is mounted in a holder 43. The object 6, to be inspected, is held by a carrier 45 so that the surface 5 of the object 6 faces a first side face 43A of the holder 43. The configurable area light source 2 is mounted to a second side face 43B of the holder 43 such that illumination light 10 is directed via the illumination lens 12 onto the beam splitter 4 and from there onto the surface 5 of the object 6. The light reflected from the surface 5 of the object 6 travels along the imaging beam path 81 to the camera 8. The imaging lens 7 images a field of view 13 of the surface 5 of the object 6 into the image plane 9 of the camera 8. In the embodiment shown here, two additional mirrors 82 are provided in the imaging beam path 81, in order to fold the imaging beam path 81 for space reasons. With the inventive inspection apparatus 200 it is possible to provide different light beam opening angles in one coaxial illumination setup.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

LIST OF REFERENCE NUMERALS 2 area light source; configurable area light source
$2_1, 2_2, \ldots, 2_N$ area diameter
2C center of area light source
3 light
4 beam splitter
5 surface
6 object
7 imaging lens
8 camera
9 image plane
10 light
11 diffuser plate
12 illumination lens 13 field of view
14 light emitting elements
15 point light source
16 carrier
$17_1, 17_2, \ldots, 17_N$ row
$18_1, 18_2, \ldots, 18_N$ column
$19_k, 19_2, \ldots, 19_N$ size
20 illumination optical axis
21 illumination beam path
22 collimated beam opening angle (before illumination lens)
23 concentric geometrical shape
24 portion
25 concentric circles
26 concentric rectangles
27 concentric hexagons
30 control and drive device
40 housing
41 mirror
43 holder
43A first side face
43B second side face
50 LCD
51 pixels of LCD
55 light
80 imaging optical axis
81 imaging beam path
82 mirror
83 imaging lens pupil, aperture
84 collimated beam opening angle (after imaging lens)
100 illumination system
200 inspection apparatus
D direction
α angle
β angle

The invention claimed is:

1. An illumination system for collimated illumination, comprising:
  a configurable area light source arranged in an illumination optical axis of an illumination beam path, wherein the configurable area light source is configured such that different beam shapes are settable between a first shape and a second shape in real-time wherein the first shape is different from the second shape;
  an imaging optical axis of an imaging beam path;
  at least one illumination lens positioned in the illumination beam path for directing a collimated beam onto a field of view on a surface of an object, wherein a value of an angle of incidence of the illumination optical axis of the illumination beam path equals a value of an angle of reflectance of the imaging optical axis of the imaging beam path;
  a beam splitter positioned in the illumination beam path after the at least one illumination lens:
  a mirror; and,
  a holder,
  wherein the beam splitter is mounted in the holder and the mirror is mounted to the holder such that light emitted from the configurable area light source is directed from the mirror to the at least one illumination lens.

2. The illumination system as claimed in claim 1, wherein the illumination lens is a Fresnel lens.

3. The illumination system as claimed in claim 1, wherein the beam splitter directs collimated illumination light from the configurable area light source along a redirected illumination optical axis of the illumination beam path onto the surface of the object, and wherein the imaging optical axis of the imaging beam path is coaxial with the redirected illumination optical axis of the illumination beam path.

4. The illumination system as claimed in claim 1, wherein the settable different beam shapes enable a variation of a collimated beam opening angle.

5. The illumination system as claimed in claim 1, wherein the configurable area light source is a 2-dimensional arrangement of a plurality of light emitting elements.

6. The illumination system as claimed in claim 5, wherein the plurality of light emitting elements includes a plurality of light emitting diodes.

7. The illumination system as claimed in claim 6, wherein the 2-dimensional arrangement of the plurality of light emitting elements is a matrix arrangement.

8. The illumination system as claimed in claim 1, wherein the configurable area light source comprises:
  a single light emitting element, providing a homogeneous area illumination; and
  an LCD-screen, positioned in front of the single light emitting element.

9. The illumination system as claimed in claim 8, wherein the LCD-screen comprises a plurality of individual pixels in a 2-dimensional arrangement and the individual pixels are addressable in order to change a transmittance value for the illumination light.

10. The illumination system as claimed in claim 1, further comprising:
  a control and drive device assigned to the configurable area light source so that a plurality of concentric geometrical shapes of illumination are generated in order to obtain different beam diameters.

11. The illumination system as claimed in claim 10, wherein the plurality of concentric geometrical shapes includes a plurality of concentric circles.

12. The illumination system as claimed in claim 10, wherein the plurality of concentric geometrical shapes includes a plurality of concentric rectangles.

13. The illumination system as claimed in claim 10, wherein the plurality of concentric geometrical shapes includes a plurality of concentric hexagons.

14. The illumination system as claimed in claim 6, wherein the 2-dimensional arrangement of the plurality of light emitting elements is defined by an arrangement of the plurality of light emitting elements in a plurality of concentric geometrical shapes.

15. The illumination system as claimed in claim 14, further comprising:
  a control and drive device assigned to the arrangement of the plurality of concentric geometrical shapes of the plurality of light emitting elements to drive the plurality of light emitting elements of the individual concentric geometrical shapes in order to obtain different beam diameters.

16. The illumination system as claimed in claim 15, wherein the plurality of concentric geometrical shapes is a plurality of concentric circles.

17. The illumination system as claimed in claim 15, wherein the plurality of concentric geometrical shapes is a plurality of concentric rectangles.

18. The illumination system as claimed in claim 15, wherein the plurality of concentric geometrical shapes is a plurality of concentric hexagons.

19. The illumination system as claimed in claim 1, wherein the first shape provides a first collimation angle and the second shape provides a second collimation angle different than the first collimation angle.

20. An inspection tool, comprising:
a camera, arranged in an imaging optical axis of an imaging beam path;
an imaging lens positioned in the imaging beam path for imaging at least a portion of a surface of an object into an image plane of the camera;
an illumination system with a configurable area light source, wherein the configurable area light source is arranged in an illumination optical axis of an illumination beam path and the configurable area light source is configured such that different beam shapes are settable between a first shape and a second shape in real-time wherein the first shape is different from the second shape;
at least one illumination lens positioned in the illumination beam path for directing a collimated beam onto a field of view on the surface of the object, wherein a value of an angle of incidence of the illumination optical axis of the illumination beam path equals a value of an angle of reflectance of an imaging optical axis of the imaging beam path;
a beam splitter positioned in the illumination beam path after the at least one illumination lens:
a mirror; and,
a holder,
wherein the beam splitter is mounted in the holder and the mirror is mounted to the holder such that light emitted from the configurable area light source is directed from the mirror to the at least one illumination lens.

21. The inspection tool as claimed in claim 20, wherein the beam splitter directs collimated illumination light from the configurable area light source along a redirected optical axis of the illumination beam path onto the surface of the object, and wherein the imaging optical axis of the imaging beam path is coaxial with the redirected optical axis of the illumination beam path.

22. The inspection tool as claimed in claim 21, further comprising:
a sample carrier
wherein:
the surface of the object is held by the sample carrier, and faces a first side face of the holder; and
the mirror is mounted to a second side face of the holder such that light from the configurable area light source is directed to the at least one illumination lens.

23. The inspection tool as claimed in claim 21, further comprising:
a sample carrier
wherein:
the surface of the object is held by the sample carrier, and faces a first side face of the holder; and
a second side face of the holder carries the configurable area light source so that light from the configurable area light source impinges on the beam splitter.

24. The inspection tool as claimed in claim 20, wherein the settable different beam shapes enable a variation of a collimation beam opening angle.

25. The inspection tool as claimed in claim 20, further comprising:
a plurality of light emitting elements:
positioned on a carrier in a 2-dimensional arrangement; and
defining the configurable area light source, wherein:
the plurality of light emitting elements are assigned to a control and drive device such that the light emitting elements in the plurality of light emitting elements are addressable individually and a plurality of patterns can be achieved by the configurable area light source; and
light beams generated according to a pattern in the plurality of patterns have a light beam opening angle.

26. The inspection tool as claimed in claim 25, wherein the 2-dimensional arrangement of the plurality of light emitting elements is a matrix arrangement.

27. The inspection tool as claimed in claim 20, wherein:
the configurable area light source comprises a single light emitting element, providing a homogeneous area lighting; and
a LCD screen, positioned in front of the single light emitting element.

28. The inspection tool as claimed in claim 27, further comprising:
a control and drive device, wherein the LCD-screen comprises a plurality of individual pixels in a 2-dimensional arrangement and the individual pixels are addressable by the control and drive device in order to change a transmittance value of the individual pixels.

29. The inspection tool as claimed in claim 20, further comprising:
a control and drive device assigned to the configurable area light source so that a plurality of concentric geometrical shapes of illumination are generated in order to obtain different beam diameters.

30. The inspection tool as claimed in claim 20, wherein the imaging beam path is folded at least one time for directing light from the field of view on the surface of the object onto the image plane of the camera.

31. The inspection tool as claimed in claim 20, wherein the illumination beam path is folded at least one time for directing light from the configurable area light source onto the surface of the object.

32. The inspection tool as claimed in claim 20, wherein the first shape provides a first collimation angle and the second shape provides a second collimation angle different than the first collimation angle.

33. A method for inspecting an object, comprising:
(a) directing illumination light, the illumination light defining a light beam opening angle, from a configurable area light source via a mirror mounted to a holder to an illumination lens along an illumination beam path, through a beam splitter mounted in the holder, onto a surface of an object;
(b) directing reflected light from the surface of the object along an imaging beam path;
(c) imaging the reflected light from the surface of the object with an imaging lens onto an image plane of a camera;
(d) changing the shape of the illumination light from a first shape to a second shape wherein the first shape is different from the second shape;
(e) repeating the steps a-d; and
(f) generating a field of view on the surface of the object in real time images with the first shape and the second shape, respectively.

34. The method of claim 33, further comprising:
setting different opening angles of the light beam by different light diameters which are generated by controlling and driving the configurable area light source so that a defined light diameter is achieved.

35. The method of claim 33, wherein the configurable area light source is a matrix arrangement of the plurality of light emitting elements.

36. The method of claim 33, wherein the configurable area light source comprises a single light emitting element, providing a homogeneous area lighting, and a LCD screen, positioned in front of the single light emitting element.

37. The method of claim 33, further comprising:
assigning a control and drive device to the configurable area light source so that a plurality of concentric and addressable geometrical shapes are generated in order to obtain different beam diameters.

38. The method of claim 35, further comprising:
arranging the plurality of light emitting elements in concentric geometrical shapes; and
addressing, with the control and drive device, the concentric geometrical shapes in order to obtain different beam diameters.

39. The method of claim 33, wherein the first shape provides a first collimation angle and the second shape provides a second collimation angle different than the first collimation angle.

40. An illumination system for collimated illumination, comprising:
a configurable area light source arranged in an illumination optical axis of an illumination beam path, wherein the configurable area light source is configured such that different beam shapes are settable between a first shape and a second shape in real-time wherein the first shape is different from the second shape;
a beam splitter is positioned in the illumination beam path after the at least one illumination lens, wherein the beam splitter directs collimated illumination light from the configurable area light source along a redirected illumination optical axis of the illumination beam path onto a surface of an object and an imaging optical axis of the imaging beam path is coaxial with the redirected optical axis of the illumination beam path;
at least one illumination lens positioned in the illumination beam path for directing a collimated beam onto a field of view on the surface of the object, wherein a value of an angle of incidence of the optical axis of the illumination beam path equals a value of an angle of reflectance of the optical axis of the imaging beam path;
a mirror; and,
a holder,
wherein the beam splitter is mounted in the holder and the mirror is mounted to the holder such that light emitted from the configurable area light source is directed from the mirror to the at least one illumination lens.

41. The illumination system of claim 40, further comprising:
a control and drive device assigned to the configurable area light source such that a plurality of concentric geometrical shapes are generated by the configurable area light source in order to obtain different beam diameters.

42. The illumination system of claim 40, wherein the first shape provides a first collimation angle and the second shape provides a second collimation angle different than the first collimation angle.

* * * * *